United States Patent
Zolotarsky et al.

(10) Patent No.: US 6,660,307 B2
(45) Date of Patent: Dec. 9, 2003

(54) PROCESS FOR GENERATING STABILIZED BROMINE COMPOUNDS

(75) Inventors: Vadim Zolotarsky, Springfield, NJ (US); Irina A. Ivanter, Sayreville, NJ (US); Tamara Oustinskaya, Union, NJ (US)

(73) Assignee: United States Filter Corporation, Palm Desert, CA (US)

( * ) Notice: Subject to any disclaimer, the term of this patent is extended or adjusted under 35 U.S.C. 154(b) by 128 days.

(21) Appl. No.: 09/835,686

(22) Filed: Apr. 16, 2001

(65) Prior Publication Data

US 2002/0172725 A1 Nov. 21, 2002

(51) Int. Cl.$^7$ .................. A01N 39/00; A01N 59/02; A01N 59/08; A01N 59/00; A61K 33/08
(52) U.S. Cl. ................ 424/703; 424/615; 424/663; 424/665; 424/680; 424/688; 424/723
(58) Field of Search ................ 424/667, 703, 424/722, 615, 663, 665, 680, 685

(56) References Cited

U.S. PATENT DOCUMENTS

| | | |
|---|---|---|
| 3,222,276 A | 12/1965 | Belohlav et al. |
| 3,558,503 A | 1/1971 | Goodenough |
| 4,088,550 A | 5/1978 | Malkin |
| 4,481,097 A | 11/1984 | Asano et al. |
| 4,584,084 A | 4/1986 | Asano et al. |
| 4,759,852 A | 7/1988 | Trulear |
| 4,929,424 A | 5/1990 | Meier et al. |
| 5,294,317 A | 3/1994 | Saito et al. |
| 5,385,650 A | 1/1995 | Howarth et al. |
| 5,435,896 A | 7/1995 | Hardee et al. |
| 5,679,239 A | 10/1997 | Blum et al. |
| 5,868,911 A | 2/1999 | Blum et al. |
| 5,868,913 A | 2/1999 | Hodgson |
| 6,068,861 A | 5/2000 | Moore, Jr. et al. |
| 6,165,343 A | 12/2000 | Blum et al. |
| 6,217,729 B1 | 4/2001 | Zolotarsky et al. |

FOREIGN PATENT DOCUMENTS

| | | |
|---|---|---|
| EP | 0391924 B1 | 3/1992 |
| EP | 0476862 A1 | 3/1992 |

*Primary Examiner*—Alton N. Pryor
(74) *Attorney, Agent, or Firm*—Wolf, Greenfield & Sacks, P.C.

(57) ABSTRACT

Active bromine-containing solutions are produced and stabilized by reacting bromate and bromide salt solutions with an amino-complexing agent, such as sulfamic acid or sulfamate salt. The reaction is performed at a pH of less than 1 to create a complexed hypobromate. The pH of the active bromine-containing solution is raised to between 4 and 10 by adding an alkali to improve stability. Moreover, the solution is maintained below 30° C. during the alkali addition to retain bromine equivalent activity.

69 Claims, No Drawings

PROCESS FOR GENERATING STABILIZED BROMINE COMPOUNDS

BACKGROUND OF THE INVENTION

1. Field of the Invention

The present invention relates to a method for producing and stabilizing active bromine solutions and, more particularly, to a method for producing an active bromine solution from a bromate salt solution with sulfamic acid.

2. Description of the Related Art

A typical process for producing bromine has been described. For example, European Patent Application Publication No. 476,862 teaches that an aqueous solution containing bromide ions may be electrolyzed under acidic conditions to produce a bromine solution. Also, equivalent bromine, as hypobromous acid, has been formed by electrolyzing a solution containing chloride and bromide ions as described in European Patent No. 391,924.

Other processes for producing bromine have been described, for example, by Blum et al., in U.S. Pat. Nos. 5,679,239, 5,868,911, and 6,165,343. Blum et al. teach a process for generating an aqueous active bromine solution by electrolyzing an aqueous solution containing bromide ions until bromate ions are formed and adding acid to the aqueous solution containing the bromate ions to generate an aqueous solution containing the active bromine compounds. Additionally, Belohlav et al., in U.S. Pat. No. 3,222,276, teach a bromination process which mixes metered quantities of a bromide-bromate salt solution and a mineral acid to liberate elemental bromine.

Howarth et al., in U.S. Pat. No. 5,385,650, describe a process for recovering bromine from acidic alkaline metal bromide and hydrobromic acid solutions. Howarth et al. teach that a process for recovery of bromine involving passing an electric current through an acidic solution thereby generating bromine by electrolysis to produce an electrolyzate containing bromine. Bromine may be separated from the electrolyzate as a vapor under negative pressure.

Aqueous bromine solutions are typically unstable and readily decompose. Accordingly, efforts have been focused on improving the stability of active bromine-containing solutions. For example, Goodenough et al., in U.S. Pat. No. 3,558,503, teach of a stable bromo-sulfamates composite which comprises a bromine stabilizer such as biuret, succinimide, urea and lower aliphatic mono- and di-substituted ureas, sulfamic acid and alkyl sulfonamides with the general formula $RSO_3NH_2$ with sufficient hydroxide additive to provide a pH of about 8 to about 10. Trulear, in U.S. Pat. No. 4,759,852, teaches using sulfamic acid to inhibit phosphonate decomposition in chlorine-bromine mixtures. Meier et al., in U.S. Pat. No. 4,929,424, similarly teach of a method for inhibiting the corrosion of metal surfaces in contact with halogenated water vapor by adding sulfamic acid. Also, Moore, Jr. et al., in U.S. Pat. No. 6,068,861, teach of preparing aqueous bromine solutions by mixing bromine-chloride or bromine with an aqueous solution of an alkali metal salt of sulfamic acid at a pH of at least about 7.

BRIEF SUMMARY OF THE INVENTION

The present invention is directed to a method for producing an active bromine solution comprising the steps of providing a solution comprising a bromate salt, adding an amino-complexing agent to the solution, adjusting a pH of the solution to below about 1, adding a halide salt to the solution and adjusting the pH of the solution to at least about 4.

In another embodiment, the present invention is directed to a method for producing a biocide solution comprising the steps of adding at least one of a sulfamate salt and sulfamic acid to a solution comprising a bromate salt, adding a halide salt to the solution, adding sulfuric acid to the solution to produce the biocide solution and adding sodium hydroxide to the biocide solution while maintaining the biocide solution at less than about 30° C.

In another embodiment, the present invention is directed to a biocide additive kit comprising a first solution comprising a bromate salt and a bromide salt, a second solution comprising an amino-complexing agent and a mineral acid and a third solution comprising an alkali.

In another embodiment, the present invention is directed to a process for producing an active bromine solution comprising the steps of providing a solution comprising a bromate salt, adding a halide salt to the solution, adding an amount of an amino-complexing agent to produce a bromate to amino-complexing agent molar ratio of at least about 3:1 to the solution, adding an amount of a mineral acid to adjust a pH of the solution to less than about 1, adding an amount of an alkali to raise the pH of the solution to between about 4 and about 10 and maintaining the solution at less than about 30° C.

In another embodiment, the present invention is directed to a biocide additive kit comprising a first solution comprising a bromate salt, a second solution comprising an amino-complexing agent, a third solution comprising a halide salt, a fourth solution comprising a mineral acid and a fifth solution comprising an alkali.

In another embodiment, the present invention is directed to a method for producing a biocide solution comprising the steps of adding at least one of a sulfamate salt and sulfamic acid to a solution comprising a bromate salt and a halide salt, adding sulfuric acid to produce the biocide solution and adding sodium hydroxide to the biocide solution while maintaining the biocide solution at less than about 30° C.

In another embodiment, the present invention is directed to a method for producing an active bromine solution comprising the steps of providing a solution comprising a bromate salt and a halide salt, adding an amino-complexing agent, adjusting a pH of the solution to below about 1 and adjusting the pH of the solution to at least about 4.

In another embodiment, the present invention is directed to a system for producing a biocide comprising a vessel in fluid communication with a first reservoir comprising a bromate salt solution, a second reservoir in fluid communication with the vessel and comprising an amino-complexing agent solution and a third reservoir in fluid communication with the vessel and comprising an alkali.

DETAILED DESCRIPTION

The present invention is directed to a method for producing and stabilizing active bromine-containing solution by reacting bromate and bromide salts with an amino-complexing agent at low pH and raising the pH to at least about 4. The active bromine-containing solution may be used as for the onsite-treatment of water such as industrial water wastewater, sewage, pools and hot tubs. Other uses of the generated solution would be apparent to those skilled in the art.

As used herein, an active bromine compound is meant to include brominated biocide compounds, and solutions thereof, having oxidative or biocide properties. A solution containing an active bromine compound may comprise any of hypobromous acid, HOBr, hypobromate salt such as sodium hypobromate, NaOBr, and bromine, $Br_2$, hypobromite ion, hydrogen tribromide and bromine chloride. In addition, stability is meant to be the ability of a solution to resist degradation because of aging, and, in this context, the ability to retain the initial active bromine equivalent. The active bromine equivalent of a solution may be determined by any method known in the art including, for example, iodine titration. A biocide is any substance that is toxic or lethal to living organisms, such as a pesticide, herbicide, or fungicide, and in this context, a biocide solution may be an active bromine-containing solution.

A bromate solution may be produced by electrolyzing a bromide salt, for example, sodium bromide, NaBr, in alkaline conditions to produce an aqueous solution containing bromate salts. Such a process has been described by Blum et al., in U.S. Pat. Nos. 5,679,239, 5,868,911 and 6,165,343, each of which are incorporated by reference in their entireties.

The aqueous solution containing the bromate salts may then be used to produce an active bromine-containing solution. Typically, the bromate salt containing solution also comprises halide salts. Preferably, the halide is a bromide salt such as sodium bromide. If a mineral acid, for example, sulfuric, hydrochloric or phosphoric acid, is used to acidify the bromate/halide salt solution, the resulting solution will be an acidic solution containing bromine. However, if an amino-complexing agent is added to the bromate/halide salt-containing solution that has been acidified, the resulting solution will contain an active bromine compound such as hypobromous acid because, it is believed, the amino-complexing agent forms a stable complex with the hypobromous acid. It is believed that the conversion of the bromate to an active bromine compound proceeds according to the following reaction:

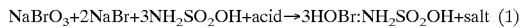

$$NaBrO_3+2NaBr+3NH_2SO_2OH+acid \rightarrow 3HOBr:NH_2SO_2OH+salt \quad (1)$$

The amino-complexing agent is typically a compound of the general formula $NH_2SO_3R$ where R may be H, OH or any alkyl, alkene or alkane, for example, $CH_3$ and $C_2H_5$. In preferred embodiments, the amino-complexing agent is any of sulfamic acid, $NH_2SO_2OH$, and a sulfamate salt such as sodium sulfamate, $NaOSO_2NH_2$ and ammonium sulfamate, $NH_4OSO_2NH_2$. Accordingly, if sulfamic acid or sulfamate is used as the amino-complexing agent, the complexed hypobromous acid may be referred to as bromosulfamate, as described by Goodenough et al. in U.S. Pat. No. 3,558,503 which is incorporated herein by reference in its entirety.

In a preferred embodiment, the amino-complexing agent is added in an amount corresponding to at least about 3 moles of amino-complexing agent per mole of bromate salt and, more preferably, the ratio of amino-complexing agent to bromate salt is about 3.3:1, and even more preferably, 3.6:1.

In another embodiment, the amino-complexing agent is added to a solution comprising a bromate salt and having a pH of less than about 2, more preferably, less than about 1. The acidic conditions are necessary, it is believed, to initiate reaction (1) and to increase the rate of reaction. For example, if the pH is maintained above about 1, reaction (1) typically requires at least about 20 hours. However, if the pH is less than about 1, then reaction (1) proceeds essentially to completion in less than about 3 hours. The pH of the bromate salt containing solution may be lowered to less than about 1 by adding a sufficient amount of a mineral acid such as sulfuric acid or hydrochloric acid.

Adjusting the pH to between about 4 and about 10 further stabilizes the active bromine-containing solution. If the pH greater is than about 10, it is believed, in alkaline solutions, the hypobromous acid may form sodium hypobromate which may in turn disproportionate into sodium bromate according to the following reaction:

$$HOBr+NaOH \rightarrow NaOBr+H_2O \quad (2)$$

$$3NaOBr \rightarrow NaBrO_3+2NaBr \quad (3)$$

Notably, this is essentially the reverse reaction of reaction (1) described above. Accordingly, after reaction (1) has proceeded, the pH of the active bromine-containing solution is adjusted to preferably at least about 4 and less than about 10 and, more preferably, less than about 8. The pH of the active bromine-containing solution may be adjusted by adding an alkali, for example, an alkaline earth hydroxide or an alkaline metal hydroxide. For example, sodium hydroxide as a solution or as a solid may be added to adjust the pH. In a preferred embodiment, the pH is adjusted to at least about 4 within about four days after reaction (1), preferably within 3 days, more preferably, within 2 days and even more preferably, within one day. Other examples of alkali include, but not limited to, calcium hydroxide, ammonium hydroxide, lithium hydroxide, potassium hydroxide, magnesium hydroxide.

If the temperature is not maintained at less than about 30° C., the active bromine content of the solution decreases because of exothermic reaction associated with raising the pH of the solution promotes an undesirable reaction, it is believed according to:

$$2NaOBr \rightarrow 2NaBr+O_2 \quad (4)$$

The temperature of the active bromine-containing solution may be maintained by techniques known in the art, for example, by using a jacketed vessel wherein a temperature controlled cooling water circulates through the vessel jacket or by use of a heat exchanger either immersed within the active bromine-containing solution and having temperature controlled cooling water circulating through the heat exchanger or by circulating a portion of the active bromine-containing solution through a heat exchanger in thermal communication with temperature controlled cooling water. Preferably, the temperature of the active bromine containing solution is maintained by a temperature control system. The temperature control system may comprise a temperature sensor, such as a thermocouple, a controller and a heating medium, a cooling medium or a combination thereof. Accordingly, in another embodiment, the temperature of the active bromine-containing solution is maintained at a temperature of less than about 30° C., more preferably less than about 25° C., and even more preferably less than about 20° C.

In another embodiment, the invention comprises a system comprising a vessel with inlet streams for a bromate salt solution, a halide salt solution, an amino-complexing agent solution, an acid solution and an alkali solution. The vessel preferably has an agitation system designed to mix the vessel contents. For example, the agitation system may comprise an impeller having a variety of configurations or a forced circulation system that withdraws a portion of the vessel contents and forcibly returns the contents into the vessel to promote mixing. In another embodiment, two or more inlet streams may be combined before the solutions are introduced into the vessel. For example, the inlet streams for the bromate solution and the halide salt solutions may be combined into a single inlet stream. In another embodiment, the vessel further comprises a temperature control system. The temperature control system may comprise a heating or cooling element and, optionally, a control system comprising a temperature indicator or sensor. In another embodiment, the agitation system incorporates a temperature control system. For example, the agitation system may be a forced circulation system with a heat exchanger. In this way, the contents of the vessel are agitated while the temperature is adjusted. Furthermore, those skilled in the art can realize that the inlet streams may be fluidly connected to the forced circulation system, the vessel or both.

The system may further have an outlet port, for example, when the vessel is used in a continuous operation. The outlet port may be introduced to a water that is to be disinfected. Accordingly, the outlet port may be connected to a treatment system including, for example, recirculating cooling water systems, waste water systems, pond water, swimming pools, metal extraction systems and bleaching systems. The outlet stream can be fluidly connected to the agitation system, the vessel or both. In another embodiment, the outlet stream may be connected to an inlet stream. In yet another embodiment, the system includes elements capable of monitoring the process conditions or operating parameters and typically referred to as sensors, indicators or meters. Such process monitoring elements are known in the art and include, but are not limited to, pressure indicators, level indicators, pH meters, temperature sensors and composition analyzers.

The present invention may be further understood in light of the following examples, which are illustrative in nature and are not to be considered as limiting the scope of the invention.

EXAMPLE 1

An aqueous solution comprising sodium bromate and sodium bromide was prepared. Sulfamic acid was added to the solution in an amount sufficient to produce a sulfamic acid to sodium bromate molar ratio of about 3.3:1 to about 3.6:1. Sufficient sulfuric acid was then added to the solution until the pH was less than about 1.

Notably, sulfamic acid may be used to lower the pH of the solution instead of the mineral acid. Moreover, the order of acid addition is essential. Thus, a mixture of sulfamic and a mineral acid may be added together or the sulfamic acid must be added before the mineral acid.

The concentration of the hypobromous acid in the resultant solution was noted to be limited by the solubility of sodium bromate in the bromate/bromide mix. In particular, the solubility of sodium bromate in water is about 160 gm/l. In addition, the concentration of the hypobromous acid was limited by the solubility of sulfamic acid. Notably, the solubility of sulfamic acid in water is about 150 gm/l. The resultant solution produced, according to reaction (1), a slightly fuming yellow solution with a strong bromine odor with a hypobromous acid concentration of about 8% as active bromine by weight. It should be noted that active bromine concentration in the resultant solution can be increased by replacing sulfamic acid with sulfamic salt, which has much higher solubility than sulfamic acid.

For example, a separate solution was prepared by adding sulfamic acid and sulfuric acid with a sodium sulfamate/sulfuric acid mix to the sodium bromate solution. The resultant concentration of the hypobromous acid was noted to be about 25% greater than the concentration in the solution prepared above. The hypobromous acid concentration illustrates this concentration dependency. This solution was also a slightly fuming yellow solution with a strong bromine odor.

EXAMPLE 2

In this example, the stability of the active bromine-containing solution was evaluated. Stabilized active bromine-containing solution prepared as in Example 1 was diluted with deionized water to produce a solution with active bromine concentration of about 36.7 ppm. Separately, a solution with 17 ppm of active bromine was prepared. This latter solution was not stabilized with sulfamic acid. Both solutions, transferred into clear glass bottles, were left to stand in ambient conditions, away from direct sunlight. The active bromine content was periodically analyzed by iodine titration. Table 1 summarizes results.

TABLE 1

|  | Day 1 | Day 2 | Day 3 | Day 5 | Day 20 |
| --- | --- | --- | --- | --- | --- |
| 36.7 ppm stabilized | 100% | — | 96% | 93% | 80% |
| 17 ppm not stabilized | 100% | 50% | — | 2% | 0% |

Table 1 shows that the stabilized active bromine-containing solution retained at least 80% relative active bromine activity up to about Day 20 whereas the unstabilized solution rapidly decayed. However, it should be noted that over a period of about three days, the color of the undiluted stabilized active bromine solution prepared in Example 1 gradually changed from yellow to reddish indicating that the predominant active bromine species changed from HOBr to $Br_2$. Also, on the fourth day, this solution became rapidly unstable and released gas that was believed to be oxygen produced according to reaction (4).

EXAMPLE 3

In this example, the pH of the stabilized active bromine-containing solution prepared in Example 1 was raised to at least about 4 by adding an alkali, sodium hydroxide. If the temperature was not maintained to less than about 30° C. when the sodium hydroxide was added, the equivalent active bromine content decreased by about 5% to about 10% because, it is believed, the exothermic caustic addition reaction raised the temperature sufficiently to change the sodium hypobromate to sodium bromide and oxygen. Thus, the temperature of the active bromine-containing solution was maintained at less than about 30° C. during the sodium hydroxide addition. The stabilized active bromine-containing solution at a pH of between about 4 to about 8 had an initial active bromine equivalent of about 58,000 ppm. After one week, there were no changes found in the active bromine concentration.

Further modifications and equivalents of the invention herein disclosed will occur to persons skilled in the art using no more than routine experimentation and all such modifications and equivalents are believed to be within the spirit and scope of the invention as defined by the following claims.

What is claimed is:

1. A method for producing an active bromine solution comprising:

providing a solution comprising a bromate salt;

adding an amino-complexing agent to the solution;

adjusting a pH of the solution to below about 1;
adding a halide salt to the solution; and
adjusting the pH of the solution to at least about 4.

2. The method as in claim 1, further comprising the step of maintaining the solution at less than about 30° C.

3. The method as in claim 1, wherein the amino-complexing agent is at least one of a sulfamate salt and sulfamic acid.

4. The method as in claim 3, wherein the sulfamic acid is added until a molar ratio of bromate to sulfamic acid is at least about 3:1.

5. The method as in claim 1, wherein the amino-complexing agent is added until a molar ratio of bromate to amino-complexing agent is at least about 3:1.

6. The method as in claim 1, wherein the step of adjusting the pH of the solution to at least about 4 comprises adding an alkali.

7. The method as in claim 6, wherein the alkali is at least one of sodium hydroxide, calcium hydroxide, ammonium hydroxide, lithium hydroxide, potassium hydroxide, and magnesium hydroxide.

8. The method as in claim 6, wherein the pH is adjusted to less than about 10.

9. The method as in claim 8, wherein the pH is adjusted to less than about 8.

10. The method as in claim 1, wherein the solution has an active bromine equivalent of at least about 8%.

11. The process according to claim 1, wherein the step of adjusting a pH of the solution to below about 1 comprises adding sulfuric acid.

12. The method as in claim 1, wherein the bromate salt comprises sodium bromate.

13. The method as in claim 1, wherein the step of adjusting a pH of the solution to below about 1 comprises adding a mineral acid comprising sulfuric acid.

14. The method as in claim 1, wherein the amino-complexing agent comprises sulfamic acid.

15. A method for producing a biocide solution comprising:
adding at least one of a sulfamate salt and sulfamic acid to a solution comprising a bromate salt;
adding a halide salt to the solution;
adding sulfuric acid to the solution to produce the biocide solution; and
adding sodium hydroxide to the biocide solution while maintaining the biocide solution at less than about 30° C.

16. The method as in claim 15, wherein the step of adding sulfuric acid adjusts a pH of the solution to less than about 1.

17. The method as in claim 15, wherein the step of adding at least one of a sulfamate salt and sulfamic acid adjusts a pH of the solution to less than about 1.

18. The method as in claim 15, wherein the step of adding sodium hydroxide adjusts a pH of the biocide solution to at least about 4.

19. The method as in claim 18, wherein the pH of the biocide solution is less than about 10.

20. The method as in claim 19, wherein the pH of the biocide solution is less than about 8.

21. The method as in claim 15, wherein the step of adding at least one of a sulfamate salt and sulfamic acid results in a bromate to at least one of a sulfamic acid or sulfumate salt molar ratio of at least about 3:1.

22. The method as in claim 15, wherein the biocide solution has an active bromine equivalent of at least about 8%.

23. The method as in claim 15, wherein the halide salt comprises sodium bromide.

24. A biocide additive kit comprising:
a first solution comprising a bromate salt and a bromide salt;
a second solution comprising an amino-complexing agent and a mineral acid; and
a third solution comprising an alkali.

25. The kit as in claim 24, further comprising a temperature control system.

26. The kit as in claim 24, wherein the amino-complexing agent is at least one of sodium sulfamate and sulfamic acid.

27. The kit as in claim 24, wherein the mineral acid is at least one of sulfuric acid, hydrochloric acid and phosphoric acid.

28. The kit as in claim 24, wherein the alkali is at least one of sodium hydroxide, calcium hydroxide, ammonium hydroxide, lithium hydroxide, potassium hydroxide, and magnesium hydroxide.

29. The kit as in claim 24, further comprising a fourth solution formed by combining the first solution and the second solution.

30. The kit as in claim 29, wherein the fourth solution has a bromate to amino-complexing agent molar ratio of at least about 3:1.

31. The biocide additive kit as in claim 24, wherein the bromate salt comprises sodium bromate.

32. The biocide additive kit as in claim 24, wherein the bromide salt comprises sodium bromide.

33. A process for producing an active bromine solution comprising the steps of:
providing a solution comprising a bromate salt;
adding a halide salt to the solution;
adding an amount of an amino-complexing agent to produce a bromate to amino-complexing agent molar ratio of at least about 3:1 to the solution;
adding an amount of a mineral acid to adjust a pH of the solution to less than about 1;
adding an amount of an alkali to adjust the pH of the solution to between about 4 and about 10; and
maintaining the solution at less than about 30° C.

34. The process according to claim 33, wherein the step of adding an amount of an alkali adjusts the pH to between about 4 and about 8.

35. The process according to claim 33, wherein the amino-complexing agent is at least one of a sulfamate salt and sulfamic acid.

36. The process according to claim 33, wherein the mineral acid is at least one of sulfuric acid, hydrochloric acid and phosphoric acid.

37. The process according to claim 33, wherein the alkali is at least one of sodium hydroxide, calcium hydroxide, ammonium hydroxide, lithium hydroxide, potassium hydroxide, and magnesium hydroxide.

38. The process as in claim 33, wherein the bromate salt comprises sodium bromate.

39. A biocide additive kit comprising:
a first solution comprising a bromate salt;
a second solution comprising an amino-complexing agent;
a third solution comprising a halide salt;
a fourth solution comprising a mineral acid; and
a fifth solution comprising an alkali.

40. The kit as in claim 39, further comprising a temperature control system.

41. The kit as in claim 39, wherein the amino-complexing agent is at least one of a sulfamate salt and sulfamic acid.

42. The kit as in claim 39, wherein there mineral acid is at least one of sulfuric acid, hydrochloric acid and phosphoric acid.

43. The kit as in claim 39, wherein the alkali is at least one of sodium hydroxide, calcium hydroxide, ammonium hydroxide, lithium hydroxide, potassium hydroxide, and magnesium hydroxide.

44. The kit as in claim 39, further comprising a sixth solution formed by combining any of the first, second, third and fourth solutions.

45. The kit as in claim 44, wherein the sixth solution has a bromate to amino-complexing agent molar ratio of at least about 3:1.

46. The kit as in claim 39, further comprising a sixth solution formed by combining the first, second and third solutions.

47. The kit as in claim 46, wherein the sixth solution has a bromate to amino-complexing agent molar ratio of at least about 3:1.

48. The biocide additive kit as in claim 39, wherein the bromate salt comprises sodium bromate.

49. The biocide additive kit as in claim 39, wherein the halide salt comprises sodium bromide.

50. A method for producing a biocide solution comprising:
adding at least one of a sulfamate salt and sulfamic acid to a solution comprising a bromate salt and a halide salt;
adding sulfuric acid to produce the biocide solution; and
adding sodium hydroxide to the biocide solution while maintaining the biocide solution at less than about 30° C.

51. The method as in claim 50, wherein the step of adding the sulfuric acid adjusts a pH of the solution less to than about 1.

52. The method as in claim 50, wherein the step of adding the sodium hydroxide adjusts a pH of the solution to at least about 4.

53. The method as in claim 52, wherein the pH of the solution is between about 4 and about 10.

54. The method as in claim 52, wherein the pH of the solution is between about 4 and about 8.

55. The method as in claim 50, wherein the bromate salt comprises sodium bromate.

56. The method as in claim 50, wherein the halide salt comprises sodium bromide.

57. A method for producing an active bromine solution comprising:
providing a solution comprising a bromate salt and a halide salt;
adding an amino-complexing agent to the solution;
adjusting a pH of the solution to below about 1; and
adjusting the pH of the solution to at least about 4.

58. The method as in claim 57, wherein the halide salt is at least one of a bromide salt and a chloride salt.

59. The method as in claim 57, wherein the amino-complexing agent is at least one of a sulfamate salt and sulfamic acid.

60. The method as in claim 57, wherein the step of adding an amino-complexing agent results in a bromate to amino-complexing agent molar ratio is at least about 3:1.

61. The method as in claim 57, wherein the bromate salt comprises sodium bromate.

62. The method as in claim 57, wherein the halide salt comprises sodium bromide.

63. A system for producing a biocide comprising:
a vessel in fluid communication with a first reservoir comprising a bromate salt solution;
a second reservoir in fluid communication with the vessel and comprising an amino-complexing agent solution;
a third reservoir in fluid communication with the vessel and comprising an alkali; and fourth reservoir in fluid communication with the vessel and comprising a mineral acid.

64. The system as in claim 63, wherein the vessel further comprises a temperature control system.

65. The system as in claim 63, wherein the mineral acid is at least one of sulfuric acid, hydrochloric acid and phosphoric acid.

66. The system as in claim 63, wherein the alkali is at least one of sodium hydroxide, calcium hydroxide, ammonium hydroxide, lithium hydroxide, potassium hydroxide, and magnesium hydroxide.

67. The system as in claim 63, wherein the amino-complexing agent is at least one of a sulfamate salt and sulfamic acid.

68. The system as in claim 63, further comprising an outlet fluidly connected to the vessel and a water treatment system.

69. The system as in claim 63, wherein the bromate salt solution comprises sodium bromate.

* * * * *